(12) United States Patent
Cooper et al.

(10) Patent No.: US 9,844,596 B2
(45) Date of Patent: Dec. 19, 2017

(54) COMPOSITIONS FOR DEPOSITING AGENTS USING HIGHLY VOLATILE SILICONE SOLVENTS

(71) Applicant: Thompson Cooper Laboratories, LLC, Horsham, PA (US)

(72) Inventors: Eugene R. Cooper, Berwyn, PA (US); Eric R. Thompson, Horsham, PA (US)

(73) Assignee: THOMPSON COOPER LABORATORIES, LLC, Horsham, PA (US)

( * ) Notice: Subject to any disclaimer, the term of this patent is extended or adjusted under 35 U.S.C. 154(b) by 63 days.

(21) Appl. No.: 14/104,420

(22) Filed: Dec. 12, 2013

(65) Prior Publication Data

US 2014/0199249 A1 Jul. 17, 2014

Related U.S. Application Data

(63) Continuation of application No. PCT/US2012/042993, filed on Jun. 18, 2012.

(60) Provisional application No. 61/498,553, filed on Jun. 18, 2011.

(51) Int. Cl.

| | | |
|---|---|---|
| A61K 47/24 | (2006.01) |
| A61K 8/58 | (2006.01) |
| A61Q 17/00 | (2006.01) |
| A61Q 17/04 | (2006.01) |
| A61Q 19/00 | (2006.01) |
| A61K 8/891 | (2006.01) |
| A01N 25/02 | (2006.01) |
| A01N 25/24 | (2006.01) |
| A01N 33/12 | (2006.01) |

(52) U.S. Cl.
CPC ............ *A61K 47/24* (2013.01); *A01N 25/02* (2013.01); *A01N 25/24* (2013.01); *A01N 33/12* (2013.01); *A61K 8/585* (2013.01); *A61K 8/891* (2013.01); *A61Q 17/00* (2013.01); *A61Q 17/04* (2013.01); *A61Q 19/00* (2013.01); *A61Q 19/005* (2013.01)

(58) Field of Classification Search
None
See application file for complete search history.

(56) References Cited

U.S. PATENT DOCUMENTS

| | | | |
|---|---|---|---|
| 5,916,548 A | 6/1999 | Hutchins et al. | |
| 5,945,093 A * | 8/1999 | Duvel | A61K 8/42 424/70.11 |
| 2003/0165546 A1* | 9/2003 | Resch | A61K 8/34 424/401 |
| 2003/0232030 A1 | 12/2003 | Lu et al. | |
| 2003/0235553 A1 | 12/2003 | Lu et al. | |
| 2004/0192845 A9 | 9/2004 | Yu | |
| 2005/0232893 A1* | 10/2005 | Kaharu | A61K 8/42 424/70.27 |
| 2006/0211820 A1* | 9/2006 | Jonn et al. | 525/100 |
| 2007/0037732 A1 | 2/2007 | Heltovics et al. | |
| 2008/0226584 A1 | 9/2008 | Krishnan | |
| 2009/0041694 A1 | 2/2009 | Pinzer et al. | |
| 2009/0053159 A1* | 2/2009 | Brun | A61K 8/26 424/70.12 |
| 2009/0186943 A1 | 7/2009 | Ikeda et al. | |
| 2010/0310492 A1 | 12/2010 | Stalet et al. | |

FOREIGN PATENT DOCUMENTS

| | | |
|---|---|---|
| EP | 2077123 A1 | 7/2009 |
| WO | 2010063988 A1 | 6/2010 |
| WO | 2011056115 A1 | 5/2011 |

OTHER PUBLICATIONS

Klykken, P., et al., "Silicone Film-Forming Technologies for Health Care Applications," Dow Corning, 2009.

* cited by examiner

*Primary Examiner* — Brian Gulledge
(74) *Attorney, Agent, or Firm* — Elmore Patent Law Group, P.C.; Edgar Harlan; Carolyn Elmore

(57) ABSTRACT

The invention relates to the field of depositing agents on surfaces using highly volatile silicone solvents. Particularly, the invention relates to novel compositions useful for depositing agents on skin and other surfaces.

**

COMPOSITIONS FOR DEPOSITING AGENTS USING HIGHLY VOLATILE SILICONE SOLVENTS

RELATED APPLICATIONS

This application is a continuation of International Application No. PCT/US12/042993, which designated the United States and was filed on Jun. 18, 2012, which claims the benefit of U.S. Provisional Application No. 61/498,553, filed on Jun. 18, 2011. The entire teachings of the above applications are incorporated herein by reference.

FIELD OF THE INVENTION

The invention relates to the field of quickly and efficiently depositing agents, and films containing agents onto skin and other biological surfaces using highly volatile silicone compositions, which compositions are capable of depositing a variety of such agents, including germicidal/antimicrobial/sanitizing agents, skin conditioning and/or protective agents, sunscreen agents, and others. Particularly, the invention relates to such novel compositions, and with additional optional ingredients such as fragrances, colorants, and the like.

BACKGROUND OF THE INVENTION

The vehicles for application of materials to skin overwhelmingly tend to be in the form of aqueous-based systems. In such systems the materials to be applied are either in solution or suspension and can be thickened to create gels, lotions, and creams. Although water is volatile, it takes considerable time to evaporate, especially for creams. Such aqueous-based systems require the use of preservatives and can require considerable time to "rub-in". The least common application system for skin is an ointment or paste, which is messy and leaves a residual layer of viscous, tacky material. There is a need to deliver materials to skin in such a way as to avoid preservatives, odors (such as alcohols), and the potential for cooling, burning, and stinging (such as is found with alcohols), substantially free of water. There is also a need to complete the application process in a short time, such as in a few seconds, and to apply materials in such a way as to leave the skin feeling smooth and not tacky.

Sanitizer products are known in the art which sanitize skin and a variety of surfaces to render them germ-free. Germicidal products range from spray solutions to bactericidal hand soaps. These products evidence the desire of people to maintain germ-free environments, minimizing exposure to harmful bacteria and other microorganisms, by depositing chemicals on surfaces which kill such organisms. In addition to the desire to sanitize such surfaces as kitchen counters, bathroom sinks, toilet seats, and the like, it would also be desirable to retain the germicidal chemical on the surface to maintain sanitizing character to the surface for an extended period of time. There are numerous products (see for example www.artandopinion.com/2007_v6_n6/glaser-triclosan.html) that contain the chemical triclosan, and agents such as tea tree oil or benzalkonium chloride, which are known to kill microorganisms. Perhaps the most common surface sanitizer is one that contains alcohol in a gel or spray formulation. Alcohol-based products tend to dry the skin, they can burn and sting, and they do not retain antimicrobial activity. These and other products also require considerable time for "rubbing in" or "drying" of the formulation.

There is a need in the art to deposit antimicrobial agents on surfaces not only to sanitize the surface of harmful microorganisms, but advantageously to retain such agent on the surface in order to provide sanitizing conditions to the surface for an extended period of time.

Skin conditioning agents are typically applied as lotions or creams, which are aqueous based and require preservatives and "rub in" to evaporate the water. There is a need to apply conditioning materials to skin without water and which requires only a few seconds and can leave conditioning agents on skin. Likewise, there is a need to apply such agents as sunscreens in highly retentive films in a matter of seconds.

The art is in need of superior compositions, substantially free of water, and free of the problems of today's known film-depositing compositions.

SUMMARY OF THE INVENTION

The disadvantages of both aqueous based systems and alcohol based systems can be avoided by using a nonaqueous delivery system based on highly volatile silicone fluids (such as hexamethyldisiloxane and octamethyltrisiloxane) as the highly volatile carrier for a myriad of materials. Such systems can be used to deliver antimicrobial agents, skin conditioning agents, retentive polymers, skin feel agents, skin protective agents, and other materials in a fluid that spreads and evaporates in a few seconds. Such systems can be sprayed onto skin without rubbing, which is a particular advantage for persons applying materials to legs and feet and where touching is undesirable. Elderly persons, for example, have particular difficulty bending over and rubbing topical products on their legs and feet, and these systems allow for the elderly to apply beneficial agents such as sanitizers and skin conditioning agents rapidly and without rubbing or having to reach their feet. In another aspect, a highly viscous and tacky polymer such as a high molecular weight silicone polymer can be applied as a skin protectant for diaper rash prevention in a few seconds, leaving the skin smooth and non-tacky, as contrasted to the highly viscous and sticky pastes that are commonly used. Compositions of the invention can advantageously be applied to broken skin such as abrasions without pain and touching. Agents can thereby be delivered to the skin in a few seconds leaving behind the agents or a thin film containing the desired agent, from antimicrobial protection and skin conditioning, to sunscreen protection and others.

One aspect of the invention provides delivery of sanitizer/antimicrobial ingredients to a surface with a system that does not contain high levels of alcohol, and which can be applied within 5 seconds or less. Furthermore this system can provide for the retention of the sanitizer as well as extended protection for the surface or skin, and it may contain other agents for conditioning and lubricating skin as well as other cosmetically desired ingredients. Such a system may be a non-viscous fluid that can be sprayed onto a surface that deposits within a few seconds a thin film of sanitizing formulation with or without rubbing. Thus it may easily and rapidly be used for application to feet and other surfaces which are hard to reach. The system can also be applied to a variety of surfaces, such as leather, wood, clothing, and the like, without the disadvantages associated with aqueous and alcohol-based products. The present invention thereby overcomes the problems of known sanitizer compositions. Particularly, the invention permits the delivery of sanitizer ingredients to a surface wherein the sanitizer composition avoids the disadvantages of known sanitizer compositions, (e.g., does not burn, sting, or dry the skin), and which can be applied quickly (e.g., within 5 seconds or less) without the need to "rub in". Furthermore the compositions of the invention are capable of providing for the retention of the sanitizer on the surface (skin or other surfaces) and thereby maintain sanitizing protection for the skin and other surfaces.

The invention includes compositions and methods for delivering a sanitizing agent (e.g., benzalkonium chloride) to a surface to not only sanitize the surface but to provide sanitization for an extended period of time. The agent optionally may be applied in a thin film; more specifically, the invention provides the ability to deliver such a film via a liquid that can be sprayed or placed on a surface by using a highly volatile solvent such that the film can be formed/spread quickly and conveniently. For example, such a system can be sprayed onto the skin, on household surfaces, or even animals (and either be spread or not) and it will dry within a few seconds to provide a thin film that is invisible but yet which can provide extended sanitization for several hours.

In one aspect, the invention provides a composition containing benzalkonium chloride dissolved in a highly volatile silicone liquid optionally containing a film-forming silicone polymer. Spraying a small quantity of such a sanitizer composition onto skin will deposit within a few seconds a thin film containing benzalkonium chloride such that the skin retains its smooth feel despite the fact that the thin sanitizing film remains thereon. This system provides a rapid and convenient way to provide immediate and long-lasting sanitization protection. Other suitable germicidal agents may be used, alone or in combination, such as alkyl quaternary ammonium germicides (including benzethonium chloride), lauric acid, undecylenic acid, and the like.

In other aspects of the invention, other optional desirable ingredients may be included and deposited in a like manner and in combination. Thus, in some aspects, the compositions of the invention may contain other additional ingredients such as skin conditioners, local anesthetics (e.g., lidocaine and the like), sunscreens, insect repellents, fragrances, colorants, drugs, nutrients, and vitamins. Such a sanitizing composition is generally a non-viscous fluid that can be sprayed onto a surface, depositing within a few seconds a very thin film of sanitizing formulation without rubbing, although rubbing is optional. Thus it may easily and rapidly be used for application to feet and other hard to reach surfaces. The compositions of the invention may advantageously be applied to a wide variety of ordinary items, such as leather, wood, clothing, etc., without the problems associated with other aqueous and alcohol-based products.

In still other aspects of the invention, the composition does not include a sanitizing agent, but instead contains such skin conditioners, local anesthetics (e.g., lidocaine and the like), sunscreens, insect repellents, fragrances, colorants, drugs, nutrients, and vitamins. Any combination of such ingredients may be aspects of the invention.

Thus, in one aspect, the invention provides a composition for depositing an agent to a surface, the composition comprising an effective amount of the agent, a highly volatile silicone solvent, and optionally a film-forming polymer. The solvent may be selected from hexamethyl disiloxane and octamethyl trisiloxane, and others. The polymer may be a polydimethylsiloxane (50,000 cSt or greater). The highly viscous silicone polymers are highly sticky and tacky but surprisingly when applied according to the invention, the skin feels lubricated and the film is highly retentive and protective, particularly from water-soluble irritants. The agent may be selected from a germicide, a skin conditioner/protectant, and a sunscreen, or others.

In a germicidal aspect of the invention, the germicide may be selected from benzalkonium chloride, benzethonium chloride, lauric acid, and undecylenic acid.

In a skin conditioner/protectant aspect of the invention, the skin conditioner/protectant may be selected from Croda's Liquid Medilan™ Ultra (lanolin oil (LO)), petrolatum (WP), Croda's Medilan™ USP and Medilan Ultra-lanolins, Dow Corning® Soy wax, Dow Corning® Cosmetic wax, Shea butter, dodecamethylpentasiloxane (2.0 cSt), Dow Corning® ST-Cyclomethicone 5-NF, Dow Corning® 9040, and ST Elastomer 10.

In a sunscreen aspect of the invention, the sunscreen may be octyl salicylate.

In some aspects of the invention, optional ingredients may be present in the composition, such as those selected from a local anesthetic, an insect repellent, a fragrance, a colorant, a drug, and a vitamin.

In another aspect of the invention, the composition is in a functionally useful form, such as a solution, a dispersion, a gel, and a semi-solid.

In another aspect, the invention includes a method of applying a composition of the invention by administering the composition to the desired surface, such as the skin. In some aspects, the composition is in a liquid form in a spray bottle, while other forms are readily administered by direct application.

Such aspects of the invention are generally substantially free of water.

These and other objects are achieved through the present invention as exemplified and further described in the Detailed Description of the Invention below.

DETAILED DESCRIPTION OF THE INVENTION

In general, the compositions of the invention comprise an effective amount of an agent mixed with a highly volatile silicone solvent. Optionally, the compositions may further comprise a film-forming polymer. The solvent and polymer permit the application of the agent such that the solvent rapidly evaporates, leaving a thin film comprised of the polymer and the agent.

In one embodiment, for example, a sanitizing composition of the invention contains an effective amount of a germicidal agent in a highly volatile silicone solvent. In its simplest form, the invention can be made by dissolving benzalkonium chloride, or other germicide, in a highly volatile silicone solvent such as hexamethyldisiloxane (HDS) and/or octamethyltrisiloxane. Typical levels of benzalkonium chloride are 0.13% or less. A small amount (less than about 3%) of a low molecular weight alcohol such as isopropyl alcohol or ethanol may be used to help solubilize polar germicides like benzalkonium chloride.

In order to form an invisible but retentive film which maintains the germicidal agent on the surface, a film-forming polymer may be included in the composition. These include protecting/conditioning materials such as high viscosity polydimethylsiloxanes (about 15,000 cSt and greater)—highly protective and retentive to skin. Certain skin conditioning agents that are somewhat retentive include Croda's Liquid Medilan™ Ultra (lanolin oil (LO)), petrolatum (WP), Croda's Medilan™ USP and Medilan™ Ultra-lanolins, Dow Corning® Soy wax, and Dow Corning® Cosmetic wax. Certain "skin feel" agents are also potentially retentive, such as moderately volatile silicones like dodecamethylpentasiloxane (2.0 cSt), decamethyltetrasiloxane, and Dow Corning® ST-Cyclomethicone 5-NF and gels such as Dow Corning® 9040 and ST Elastomer 10.

In other embodiments, the agent is a component such as local anesthetics, sunscreens, insect repellents, fragrances, colorants, drugs, nutrients, and vitamins.

Highly Volatile Silicone Solvents

Many highly volatile silicone solvents are suitable for use in the present invention. Hexamethyldisiloxane is one preferred such solvent, as is octamethyltrisiloxane. The compositions of the invention may have a single highly volatile silicone solvent, or may comprise a combination of more than one such solvents.

Film-Forming Polymers

In some embodiments of the invention, it is desired to maintain the activity of the agent for an extended period of time following its application. In such cases, a film-forming polymer may be included in the composition which, upon volatilization of the silicone solvent, (i.e., as the applied composition dries) forms a thin film, substantially invisible and substantially undetectable to touch, which film contains the still-active germicidal agent. Such film-forming polymers are known in the art, and include, but are not limited to, less volatile silicone compounds, such as viscous, or highly viscous silicone polymers, such as polydimethylsiloxanes (50,000 cSt or greater).

The compositions of the invention may have a single film-forming polymer, or may comprise a combination of two or more such polymers.

Germicidal Agents

Those of skill in the art will appreciate that there are many germicidal agents suitable for use in the present invention. While many of the embodiments and examples recited herein use benzalkonium chloride as the germicidal agent, such agents include all alkyl quaternary ammonium germicides, benzethonium chloride, lauric acid, undecylenic acid, and others known to those of skill in the art. Certain quaternary ammonium germicides may require alcohol to be added to the composition in order to facilitate their solubilization in the highly volatile silicone.

Skin Conditioners

In other embodiments, the composition of the invention may comprise agents directed to skin care in general included in the formulation. Thus, for example, the composition may include such agents as protecting/conditioning materials such as super high viscosity polydimethylsiloxanes (50,000 cSt-1,000,000 cSt), Croda's Liquid Medilan™ Ultra (lanolin oil (LO)), petrolatum (WP), Croda's Medilan™ USP and Medilan Ultra-lanolins, Dow Corning® Soy wax, and Dow Corning® Cosmetic wax, Shea butter and "skin feel" agents such as low volatile silicones like dodecamethylpentasiloxane (2.0 cSt) and Dow Corning® ST-Cyclomethicone 5-NF and gels such as Dow Corning® 9040 and ST Elastomer 10. The compositions of the invention may have a single conditioner, or may comprise a combination of two or more such conditioners. The compositions may be solutions or dispersions, and the dispersions may be formed in a variety of ways including but not limited to making a solution at higher temperatures followed by agitation/high shear mixing as the solution cools. Additionally one may employ methods such cavitation/microfluidization to create nano sized dispersions.

Other Agents and Optional Components

In some embodiments, optional components include local anesthetics (e.g., benzocaine), sunscreens (e.g., octyl salicylate), insect repellents (e.g., N,N,-Diethyl-meta-toluamide (DEET)), fragrances (e.g., lavender oil), colorants (e.g., beet root extract), drugs (e.g, retinol), and vitamins (e.g., nicotinamide). The compositions of the invention may have a single such optional component, or may comprise a combination of two or more such optional components. Alternatively, in some embodiments, the composition of the invention may have these otherwise optional components as the desired agent itself. For example, in one embodiment of the invention, the composition is a highly volatile silicone solvent, a film-forming polymer, and a sunscreen agent. Such a composition of the invention provides rapid and efficient application of the sunscreen to the skin. In another embodiment, for example, a sunscreen agent is added to a skin-conditioning composition of the invention, whereby the composition comprises both a skin conditioner agent and a sunscreen agent. Those of skill in the art will appreciate the many varied combinations of agents and optional ingredients made possible by the invention.

Forms of the Compositions of the Invention

In some embodiments, the composition of the invention is in the form of a liquid, generally applied in a spray bottle or other application device. In other embodiments, the invention's compositions may be formulated in a gel form, for direct application to the skin. Such gels may be prepared by using a gelling agent, such as Dow Corning® 9040 and ST Elastomer 10 added to the composition.

Uses of the Compositions of the Invention

Uses of the highly adaptable compositions of the invention are limited only by the user's imagination. Essentially any surface to be sanitized or coated is an appropriate surface for the compositions of the invention to be applied to. The embodiments of the invention with skin protectants and conditioners are highly suitable for use on skin surfaces, whether it be the hands, face, feet, etc. Such embodiments are also well-suited for other biological surfaces, but embodiments such as germicidal compositions can be applied to counters, doorknobs, leather goods, and the like; where the surface to be treated is not skin, embodiments of the invention without skin protectants and conditioners are quite suitable for extended sanitization.

Other embodiments, uses, and advantages of the present invention will be apparent to those skilled in the art from consideration of the specification and practice of the invention disclosed herein. The specification and examples should be considered exemplary only. The intended scope of the invention is only limited by the claims appended hereto.

EXAMPLES

The present invention will be further understood by reference to the following non-limiting examples.

Germicidal Compositions

Example 1: Germicidal Composition

On a weight basis 0.13% benzalkonium chloride, 2.5% isopropyl alcohol, 1.3% polydimethyl siloxane (300,000 cSt), and 96.07% hexamethyldisiloxane were mixed to form a clear solution. This solution when sprayed onto skin or other surface can be spread and dried in a few seconds to leave a smooth film containing benzalkonium chloride.

Example 2: Germicidal Composition

On a weight basis 0.13% benzalkonium chloride, 1.25% ethyl alcohol, 0.8% polydimethyl siloxane (300,000 cSt), 0.5% Dow Corning® 9040, and 97.32% hexamethyldisiloxane were mixed to form a clear solution. This solution when sprayed onto skin or other surface can be spread and dried in a few seconds to leave a smooth film containing benzalkonium chloride.

Example 3: Germicidal Composition

On a weight basis 0.13% benzalkonium chloride, 1.25% ethyl alcohol, 0.8% polydimethyl siloxane (300,000 cSt), 0.5% Dow Corning® 9040, and 97.32% hexamethyldisiloxane were mixed to form a clear solution. This solution when sprayed onto skin or other surface can be spread and dried in a few seconds to leave a smooth film containing benzalkonium chloride.

Example 4: Germicidal Composition

On a weight basis 0.13% benzalkonium chloride, 2.5% isopropyl alcohol, 1% Dow Corning® Cosmetic or Soy Wax, and 96.37% hexamethyldisiloxane were mixed to form a clear solution upon heating. This mixture became turbid upon cooling to room temperature and when sprayed onto skin or other surface can be spread and dried in a few seconds to leave a smooth film containing benzalkonium chloride.

Example 5: Germicidal Composition

On a weight basis 0.13% benzalkonium chloride, 1.25% ethyl alcohol, 1.0% polydimethyl siloxane (300,000 cSt), 1.0% Croda Liquid Medilan™ Ultra, 3% Dow Corning® ST-Cyclomethicone 5-NF, and 93.62% hexamethyldisiloxane were mixed to form a clear solution. This solution when sprayed onto skin or other surface can be spread and dried in a few seconds to leave a smooth film containing benzalkonium chloride.

Example 6: Germicidal Composition

On a weight basis 0.13% benzalkonium chloride, 1.25% ethyl alcohol, 2.3% Croda Liquid Medilan™ Ultra, 0.7% Dow Corning® 9040, 2% Dow Corning ST-Cyclomethicone 5-NF, and 93.62% hexamethyldisiloxane were mixed to form a clear solution. This slightly turbid mixture when sprayed onto skin or other surface can be spread and dried in a few seconds to leave a smooth film containing benzalkonium chloride.

Example 7: Germicidal Composition

On a weight basis 0.13% benzalkonium chloride, 1.25% ethyl alcohol, 1.0% Croda Liquid Medilan™ Ultra, 4% Dow Corning® ST-Cyclomethicone 5-NF, and 93.62% hexylmethyldisiloxane were mixed to form a clear solution. This solution when sprayed onto skin or other surface can be spread and dried in a few seconds to leave a smooth film containing benzalkonium chloride.

Example 8: Germicidal Composition

On a weight basis 0.13% benzalkonium chloride, 1.25% ethyl alcohol, 2.0% Croda Liquid Medilan™ Ultra, 3% Dow Corning® ST-Cyclomethicone 5-NF, and 93.62% hexylmethyldisiloxane were mixed to form a clear solution. This solution when sprayed onto skin or other surface can be spread and dried in a few seconds to leave a smooth film containing benzalkonium chloride.

Example 9: Germicidal Composition

On a weight basis 0.13% benzalkonium chloride, 1.25% ethyl alcohol, 3.0% Croda Liquid Medilan™ Ultra, 2% Dow Corning® ST-Cyclomethicone 5-NF, and 93.62% hexamethyldisiloxane were mixed to form a clear solution. This solution when sprayed onto skin or other surface can be spread and dried in a few seconds to leave a smooth film containing benzalkonium chloride.

Example 10: Germicidal Composition

On a weight basis 0.13% benzalkonium chloride, 1.25% ethyl alcohol, 2.0% Croda Liquid Medilan™ Ultra, 3% octamethyltrisiloxane, and 93.62% hexamethyldisiloxane were mixed to form a clear solution. This solution when sprayed onto skin or other surface can be spread and dried in a few seconds to leave a smooth film containing benzalkonium chloride.

Example 11: Germicidal Composition

On a weight basis 0.13% benzalkonium chloride, 1.25% ethyl alcohol, 5% polydimethyl siloxane (300,000 cSt), 0.2% lidocaine, and 93.42% hexamethyldisiloxane were mixed to form a clear solution. This solution can be sprayed onto a light wound or abrasion to prevent infection, control pain, and provide a protective coating.

Example 12: Germicidal Composition

On a weight basis 0.13% benzalkonium chloride, 2.5% isopropyl alcohol, 1.3% polydimethyl siloxane (300,000 cSt), 0.2% lidocaine, and 95.87% hexamethyldisiloxane were mixed to form a clear solution. This solution can be sprayed onto a light would or abrasion to prevent infection, control pain, and provide a protective coating.

Example 13: Germicidal Composition

On a weight basis 0.13% benzalkonium chloride, 1.25% ethyl alcohol, 0.2% lidocaine, and 98.42% hexamethyldisiloxane were mixed to form a clear solution. This solution can be sprayed onto a light wound or abrasion to prevent infection, control pain, and provide a protective coating.

Example 14: Germicidal Composition

On a weight basis 0.13% benzalkonium chloride, 1.25% ethyl alcohol, and 98.62% hexamethyldisiloxane were mixed to form a clear solution. This solution can be sprayed onto a surface or wound where no residue is desired. Such an example would be for example to prevent infection in animal ears.

Example 15: Germicidal Composition

On a weight basis 0.13% benzalkonium chloride, 1.25% ethyl alcohol, 2.0% Croda Liquid Medilan™ Ultra, 3.0% octamethylcyclotetrasiloxane, and 93.62% octamethyltrisiloxane were mixed to form a clear solution. This solution when sprayed onto skin or other surface can be spread and dried in a few seconds to leave a smooth film containing benzalkonium chloride.

Example 16: Germicidal Composition

On a weight basis 0.13% benzalkonium chloride, 1.25% ethyl alcohol, 2.0% Croda Liquid Medilan™ Ultra, 3.0% decamethylcyclopentasiloxane, and 93.62% hexamethyldisiloxane were mixed to form a clear solution. This solution when sprayed onto skin or other surface can be spread and dried in a few seconds to leave a smooth film containing benzalkonium chloride.

Example 17: Germicidal Composition

On a weight basis 0.13% benzalkonium chloride, 1.25% ethyl alcohol, 2.0% Croda Liquid Medilan™ Ultra, 3.0% octamethylcyclotetrasiloxane, 30% octamethyltrisiloxane, and 63.62% hexamethyldisiloxane were mixed to form a clear solution. This solution when sprayed onto skin or other surface can be spread and dried in a few seconds to leave a smooth film containing benzalkonium chloride.

Nongermicidal Compositions

Skin conditioning and moisturizing, skin protectant, and wound healing compositions without antimicrobial agents are shown in the following example compositions, which do not contain water, do not burn or sting, can be sprayed on or applied by gentle rubbing, and can be used on the face as well. They leave the skin with a very smooth and non-sticky feel.

Example 18: Skin Conditioning Compositions

The following dispersions of solid moisturizers in the highly volatile hexamethyldisiloxane were obtained by heating all ingredients till a clear solution was obtained and then gradual cooling with vigorous shaking as the dispersion forms:

18.1) By weight 10% Dow Corning® HY-3050 Soy Wax and 90% hexamethyldisiloxane were mixed and processed as described above to provide a low viscosity dispersion for rapid and even application to skin.

18.1a) By weight 10% Dow Corning® ST-Wax30 and 90% hexamethyldisiloxane were mixed and processed as described above to provide a low viscosity dispersion for rapid and even application to skin.

18.1b) By weight 10% Medilan™ Ultra Lanolin and 90% hexamethyldisiloxane were mixed and processed as described above to provide a low viscosity dispersion for rapid and even application to skin.

18.2) By weight 20% Dow Corning® ST-Wax30 and 80% hexamethyldisiloxane were mixed and processed as described above to provide a low viscosity dispersion for rapid and even application to skin.

18.2a) By weight 20% Dow Corning® HY-3050 Soy Wax and 80% hexamethyldisiloxane were mixed and processed as described above to provide a low viscosity dispersion for rapid and even application to skin.

18.2b) By weight 20% Medilan™ Ultra Lanolin and 80% hexamethyldisiloxane were mixed and processed as described above to provide a low viscosity dispersion for rapid and even application to skin.

18.3) By weight 20% Dow Corning® ST-Wax30, 10% Dow Corning® ST-Elastomer 10, and 70% hexamethyldisiloxane were mixed and processed as described above to provide a low viscosity dispersion for rapid and even application to skin.

18.3a) By weight 20% Dow Corning® HY-3050 Soy Wax, 10% Dow Corning® ST-Elastomer 10, and 70% hexamethyldisiloxane were mixed and processed as described above to provide a low viscosity dispersion for rapid and even application to skin.

18.3b) By weight 20% Medilan™ Ultra Lanolin, 10% Dow Corning® ST-Elastomer 10, and 70% hexamethyldisiloxane were mixed and processed as described above to provide a low viscosity dispersion for rapid and even application to skin.

18.4) By weight 35% Medilan™ Ultra Lanolin, 20% Dow Corning® ST-Elastomer 10, and 45% hexamethyldisiloxane were mixed and processed as described above to provide a medium viscosity dispersion for rapid and even application to skin.

18.5) By weight 45% Medilan™ Ultra Lanolin, 20% Dow Corning® ST-Elastomer 10, and 35% hexamethyldisiloxane were mixed and processed as described above to provide a viscous dispersion for rapid and even application to skin.

18.6) By weight 20% Medilan™ Ultra Lanolin, 20% Dow Corning® ST-Cyclomethicone 5-NF, and 60% hexamethyldisiloxane were mixed and processed as described above to provide a low viscosity dispersion for rapid and even application to skin.

18.7) By weight 25% Liquid Medilan™ Ultra Lanolin, 20% Dow Corning® ST-Cyclomethicone 5-NF, 2.5% beeswax, and 52.5% hexamethyldisiloxane were mixed and processed as described above to provide a low viscosity dispersion for rapid and even application to skin.

18.8) By weight 25% Liquid Medilan™ Ultra Lanolin, 20% Dow Corning® ST-Cyclomethicone 5-NF, 2.5% Dow Corning® ST-Wax30, and 52.5% hexamethyldisiloxane were mixed and processed as described above to provide a low viscosity dispersion for rapid and even application to skin.

18.9) By weight 25% Liquid Medilan™ Ultra Lanolin, 20% Dow Corning® ST-Cyclomethicone 5-NF, Dow Corning® HY-3050 Soy Wax, and 52.5% hexamethyldisiloxane were mixed and processed as described above to provide a low viscosity dispersion for rapid and even application to skin.

18.10) By weight 25% Liquid Medilan™ Ultra Lanolin, 20% Dow Corning® ST-Cyclomethicone 5-NF, 5% Dow Corning® ST-Wax30, and 50% hexamethyldisiloxane were mixed and processed as described above to provide a low viscosity dispersion for rapid and even application to skin.

Example 19: Skin Conditioning Compositions with Additional Ingredients 19.1) By weight 32% Liquid Medilan™ Ultra Lanolin, 3% Vitamin E, and 65% hexamethyldisiloxane were dissolved together to provide a low viscosity solution for rapid and even application to skin.

19.2) By weight 35% Liquid Medilan™ Ultra Lanolin, 20% Dow Corning® ST-Elastomer 10, and 45% hexamethyldisiloxane were dissolved together to provide a low viscosity hazy solution for rapid and even application to skin. (This product was given to a person who works in construction with bleeding dry hands with band aids, and after one week the hands were markedly improved with only two applications per day).

19.3) By weight 22% Liquid Medilan™ Ultra Lanolin, 3% Vitamin E, 10% Dow Corning® ST-Elastomer 10, and 65% hexamethyldisiloxane were dissolved together to provide a low viscosity hazy solution for rapid and even application to skin.

19.4) By weight 20% Liquid Medilan™ Ultra Lanolin, 20% Dow Corning® ST-Cyclomethicone 5-NF, and 60% hexamethyldisiloxane were mixed and processed as described above to provide a low viscosity solution for rapid and even application to skin.

19.5) By weight 32% Liquid Medilan™ Ultra Lanolin, 3% Vitamin E, 20% Dow Corning® ST-Cyclomethicone 5-NF, and 45% hexamethyldisiloxane were mixed and processed as described above to provide a medium viscosity solution for rapid and even application to skin.

19.6) By weight 35% Liquid Medilan™ Ultra Lanolin, 20% Dow Corning® ST-Cyclomethicone 5-NF, and 45% hexamethyldisiloxane were mixed and processed as described above to provide a medium viscosity solution for rapid and even application to skin.

Example 19a): Skin Protectant Compositions 19a.1) By weight 5% polydimethylsiloxane (300,000 cSt) and 95% hexamethyldisiloxane were mixed to give a clear solution that can be rapidly and evenly applied to lubricate and protect skin.

19a.2) By weight 5% polydimethylsiloxane (1,000,000 cSt) and 95% hexamethyldisiloxane were mixed to give a clear solution that can be rapidly and evenly applied to lubricate and protect skin.

19a.3) By weight 10% polydimethylsiloxane (300,000 cSt) and 90% hexamethyldisiloxane were mixed to give a clear solution that can be rapidly and evenly applied to lubricate and protect skin.

19a.4) By weight 10% polydimethylsiloxane (1,000,000 cSt) and 90% hexamethyldisiloxane were mixed to give a clear solution that can be rapidly and evenly applied to lubricate and protect skin.

Example 20: Sunscreen Compositions 20.1) Dissolve 5 grams octyl salicylate in 90 grams hexamethyldisiloxane and add 5 grams polydimethylsiloxane (300,000 cSt). Solution/mixture can be sprayed onto surface leaving a smooth, retentive film.

20.2) Dissolve 10 grams octyl salicylate in 80 grams hexamethyldisiloxane and add 10 grams polydimethylsiloxane (300,000 cSt). Solution/mixture can be sprayed onto surface leaving a smooth, retentive film.

20.3) Dissolve 5 grams octyl salicylate in 87 grams hexamethyldisiloxane, 3 grams cylcomethicone and add 5 grams polydimethylsiloxane (300,000 cSt). Solution/mixture can be sprayed onto surface leaving a smooth, retentive film.

20.4) Dissolve 3 grams avobenzone in 92 grams hexamethyldisiloxane and add 5 grams polydimethylsiloxane (300,000 cSt). Solution/mixture can be sprayed onto surface leaving a smooth, retentive film.

20.5) Dissolve 5 grams octyl methoxycinnamate in 90 grams hexamethyldisiloxane and add 5% polydimethylsiloxane (300,000 cSt). Solution/mixture can be sprayed onto surface leaving a smooth, retentive film.

20.6) Dissolve 7.5 grams octyl methoxycinnamatein 84.5 grams hexamethyldisiloxane and add 8 grams polydimethylsiloxane (300,000 cSt). Solution/mixture can be sprayed onto surface leaving a smooth, retentive film.

The present invention is not to be limited in scope by the specific embodiments described above, which are intended as illustrations of aspects of the invention. Functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All cited references are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A composition consisting of an alkyl quaternary ammonium germicide, a highly volatile silicone solvent, a polydimethylsiloxane having a viscosity of 50,000 cSt or greater, up to 5% of a low molecular weight alcohol and optionally one or more agents selected from skin conditioners/protectants and sunscreens.

2. The composition of claim 1, consisting of by weight 0.13% benzalkonium chloride, 2.5% isopropyl alcohol, 1.3% polydimethylsiloxane having a viscosity of 300,000 cSt, and 96.07% hexamethyldisiloxane.

3. The composition of claim 1, consisting of by weight 0.13% benzalkonium chloride, 1.25% ethyl alcohol, 1.0% polydimethylsiloxane having a viscosity of 300,000 cSt, 3% cyclomethicone, 1.0% lanolin oil and 93.62% hexamethyldisiloxane.

4. A composition consisting of by weight 0.13% benzalkonium chloride, 1.25% ethyl alcohol, 5.0% polydimethylsiloxane having a viscosity of 300,000 cSt, 0.2% lidocaine and 93.42% hexamethyldisiloxane.

5. A composition consisting of by weight 0.13% benzalkonium chloride, 2.5% isopropyl alcohol, 1.3% polydimethylsiloxane having a viscosity of 300,000 cSt, 0.2% lidocaine and 95.87% hexamethyldisiloxane.

* * * * *